United States Patent [19]
Kimball et al.

[11] Patent Number: 5,944,660
[45] Date of Patent: Aug. 31, 1999

[54] DISPOSABLE CARTRIDGE ASSEMBLY WITH OPTIONAL INTEGRATED TEMPERATURE CONTROL SYSTEM, AND SYSTEMS CONTAINING SAME

[75] Inventors: Victor E. Kimball, Burnsville; Paul J. Hindrichs, Plymouth; Brian E. Honebrink, Stillwater; Rochell S. Gifford, Minneapolis, all of Minn.

[73] Assignee: Optical Sensors Incorporated, Minneapolis, Minn.

[21] Appl. No.: 08/889,356

[22] Filed: Jul. 8, 1997

[51] Int. Cl.$^6$ .............................. A61B 5/00; G01N 21/05
[52] U.S. Cl. .............................. 600/310; 436/68; 356/39; 356/246
[58] Field of Search ................................ 600/310, 322, 600/323, 326, 316, 473, 474, 476, 529, 537, 327, 339, 341; 436/68, 164; 356/39–42, 244, 246

[56] References Cited

U.S. PATENT DOCUMENTS

| | | | |
|---|---|---|---|
| 4,786,474 | 11/1988 | Cooper | 436/68 |
| 4,791,932 | 12/1988 | Margules . | |
| 4,830,013 | 5/1989 | Maxwell . | |
| 4,871,439 | 10/1989 | Enzer et al. . | |
| 4,989,606 | 2/1991 | Gehrich et al. . | |
| 5,048,525 | 9/1991 | Maxwell . | |
| 5,058,587 | 10/1991 | Kohno et al. | 600/328 |
| 5,071,218 | 12/1991 | Nishimoto . | |
| 5,094,820 | 3/1992 | Maxwell et al. . | |
| 5,165,406 | 11/1992 | Wong . | |
| 5,216,734 | 6/1993 | Grinderslev . | |
| 5,289,255 | 2/1994 | Mullin et al. | 356/41 |
| 5,429,594 | 7/1995 | Castle | 604/4 |
| 5,442,437 | 8/1995 | Davidson | 356/246 |
| 5,455,880 | 10/1995 | Reid et al. . | |

*Primary Examiner*—Cary O'Connor
*Assistant Examiner*—Eric F. Winakur
*Attorney, Agent, or Firm*—Dianne E. Reed; Narinder S. Banait; Reed & Associates

[57] ABSTRACT

A cartridge assembly is provided for analyzing characteristics of a sample fluid. The cartridge assembly comprises an assembly body having a passageway, a cavity and, interposed between the passageway and the cavity, a manifold containing a port that serves as a feedthrough between the cavity and the passageway. The passageway forms a flow path through which the sample is drawn. The cartridge assembly also comprises a sensor responsive to a characteristic of the sample fluid. The sensor is housed in the assembly body cavity and is in communication with the passageway by way of the port in the manifold. Optionally, the cartridge assembly includes a temperature monitoring means and a heating means in thermal communication with the passageway. In addition, a method is provided in which the cartridge assembly is used for analyzing a characteristic of a sample. A bedside system for monitoring characteristics of a physiologic fluid comprising the cartridge assembly is provided as well.

13 Claims, 4 Drawing Sheets

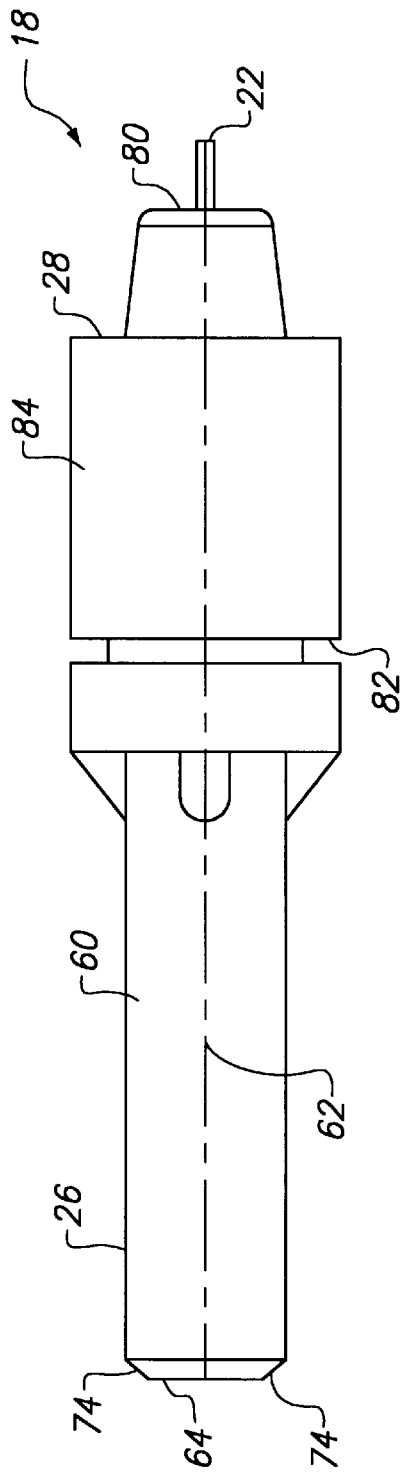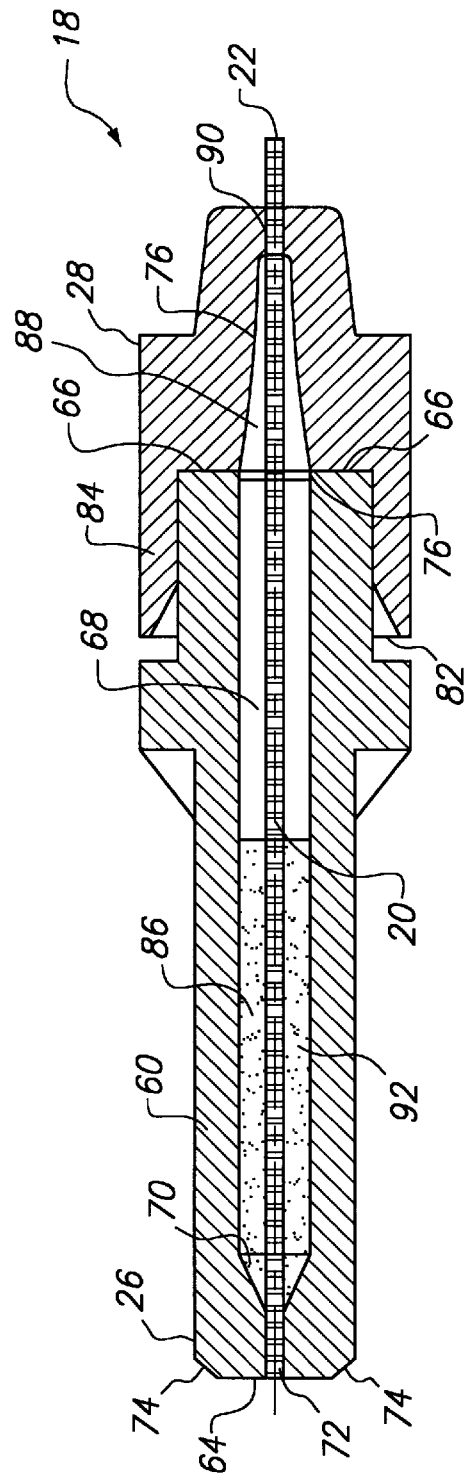

DISPOSABLE CARTRIDGE ASSEMBLY WITH OPTIONAL INTEGRATED TEMPERATURE CONTROL SYSTEM, AND SYSTEMS CONTAINING SAME

TECHNICAL FIELD

This invention relates generally to chemical sensors. More particularly, the invention relates to a cartridge assembly that houses sensors used to analyze and/or monitor characteristics of physiologic fluids such as blood. Methods for using the cartridge assembly are provided as well.

BACKGROUND

Clinical decisions regarding patient management are often made on the basis of blood chemistry analysis. A variety of procedures have been used to perform such analyses, all of which have their deficiencies.

Blood chemistry is often determined on a drawn sample of blood which is subsequently transported to an on-site facility where the analysis is performed. Blood chemistry analysis performed by such a process engenders a risk of contact with the blood sample, an increased risk to the patient of nosocomial infections and the possibility that air emboli may be introduced into the bloodstream, a potential for contamination of the sample, and, perhaps most significantly from the diagnostician's point of view, a lengthy delay between a decision that blood chemistry is necessary and delivery of therapy based on the results of the analysis.

The need for a bedside system to analyze critical blood variables (e.g., $O_2$, $CO_2$ and pH) has been addressed by placing environment-sensitive, calibrated optical or electrochemical sensors directly into a patient's artery or vein. Intraarterial or intravenous sensors are typically calibrated by immersion in a solution which has been equilibrated by bubbling with known concentrations of, for example, $O_2$ and $CO_2$, to provide a liquid with known partial pressures of $O_2$ and $CO_2$ (i.e., $pO_2$ and $pCO_2$). The ability of the sensors to detect $pO_2$ and $pCO_2$ is then compared with the known $pO_2$ and $pCO_2$.

A major disadvantage of this system is that once a calibrated sensor is inserted into a patient's blood vessel, it must be removed from the vessel for re-calibration and sterilized again before it can be re-inserted. Furthermore, it is equally difficult to perform quality control measurements to determine whether the sensors are functioning properly. Absent the ability to re-calibrate, it is extremely difficult to determine whether the system is performing properly after the sensors have been inserted. In fact, poor performance is frequently seen since (1) intraarterial or intravenous sensors are prone to thrombogenic formations which can cause serious measurement errors and (2) patient movement can result in sensor contact with the vessel wall which can also cause temporary or permanent measurement errors.

An alternative approach is an extracorporeal system or a paracorporeal system for bedside blood chemistry analysis. Extracorporeal systems have been described that house sensors sensitive to parameters in blood. Typical extracorporeal systems are described in U.S. Pat. Nos. 4,791,932 to Margules, 4,989,606 to Gehrich et al., 5,094,820 to Maxwell et al. and 5,165,406 to Wong et al. In these systems, the sensing element is located in or near the wall of the passageway through which the body fluid is passed. Such a configuration may result in inaccurate analyses of blood chemistries due to boundary layer effects. In other words, since the system is typically purged with saline or other infusion medium after each measurements, a boundary layer of medium may remain near the wall of the passageway when blood is subsequently drawn, thereby creating a concentration gradient across the lumen of the passageway. Wong et al. provides an attempt to address this problem by incorporating a helical groove in the passageway to increase turbulence therein.

A paracorporeal system places the sensors in a physiologic line (e.g., arterial or venous line) very near to a patient's arterial catheter. This approach has the primary advantages of eliminating the problems associated with thrombosis and patient movement and, in addition, provides the capability to conduct in situ calibration and quality control checks without compromising sterility. A paracorporeal design allows for a calibration to be made while the sensors are either in the physiologic line (e.g., arterial or venous line) or removed from the physiologic line (i.e., ex vivo). Moreover, quality control checks may be made at any time throughout the life of the sensors. Such a paracorporeal design is disclosed in commonly owned U.S. application Ser. No. 08/379,332, filed Jan. 27,1995, for "In Situ Calibration System for Sensors Located in a Physiologic Line," by Kimball et al., which is incorporated herein by reference.

There is a need in the art for a cartridge assembly that incorporates sensor module to accurately analyze characteristics in a sample of a physiologic fluid, such as blood, and that is capable not only of monitoring but also regulating the temperature of the sample to enhance the accuracy of the analysis.

RELATED ART

U.S. Pat. No. 5,455,880 to Reid et al. describes an optical fiber connector assembly that comprises a crimp ring having means for coupling to a connector plug, a longitudinal bore with small and large diameter portions, the large diameter portion adapted to engage a jacketed segment of cable and the small diameter portion adapted to encompass an unjacketed segment of cable. The connector plug has a bore through which the cable passes and an outlet where the cable is cleaved. The assembly is intended to be inserted into a coupling fixture either to align the cleaved end of the optical fiber cable with the end of another cable, or to an active device receptacle containing, for example, a light emitting diode.

U.S. Pat. No. 5,216,734 to Grinderslev, which is incorporated herein by reference, relates to an optical fiber ferrule assembly, for use in an optical fiber connector, that supports, positions and aligns an optical fiber in the connector for communication with a second fiber.

U.S. Pat. No. 5,071,218 to Nishimoto relates to an optical connector ferrule for positioning and securing an optical fiber cable such that the cable is mated with a second cable, stated to eliminate the disadvantages of conventional "crimp and cleave" optical connector ferrules.

SUMMARY OF THE INVENTION

Paracorporeal devices having an integral sensor assembly-cable unit have been described. However, the sensor assembly-cable unit contains unnecessary and expensive hardware, e.g., fiber optic cables, that serve merely to connect the sensor assembly-cable unit by way of a separate interconnect cable with an instrument that serves as a sensor interface and a read-out means. The present cartridge assembly integrates the functions of the sensor assembly-cable unit into a unit that can be disconnected from a reusable interconnect cable as needed, and disposed of in an appropriate manner. A fresh disposable cartridge unit can then be connected to the interconnect cable. In this way, the relatively more expensive hardware components of the device can be contained in the reusable interconnect cable. The relatively less expensive sensors, thermistors, and the like, may be contained in the single use, disposable cartridge assembly unit.

Accordingly, it is an object of the invention to provide a novel cartridge assembly for use with a paracorporeal system in which sensors may be positioned in a physiologic line. The cartridge assembly disclosed herein has the advantages of ease of manufacture and cost effectiveness. In addition, the device is fairly simple in its design.

In one aspect, then, a cartridge assembly is provided for use in an in situ system for analyzing characteristics of a physiologic fluid. The cartridge assembly comprises an assembly body having a passageway with an interior surface and terminating in distal and proximal passageway ports by which the assembly is removably connected to a physiologic line, a cavity and, interposed between the passageway and the cavity, a manifold containing a port that serves as a feedthrough between the cavity and the passageway. The passageway forms a flow path through which the physiologic fluid is drawn. The cartridge assembly also comprises a sensor responsive to a characteristic of the analyte in the physiologic fluid. The sensor is housed in the assembly body cavity and is in communication with the passageway by way of the port in the manifold. The sensor has a tip that, alternatively, is flush with the interior surface of the passageway or extends beyond the interior surface of the passageway into the flow path of the physiologic fluid The cartridge assembly also comprises means by which the sensor output may be monitored.

In another aspect of the invention, a method is provided for analyzing a characteristic of a sample. The method comprises providing a cartridge assembly as disclosed above including a sensor responsive to the characteristic of the sample, exposing the sensor to the sample, thereby producing a sensor output, monitoring the sensor output, and calculating from the sensor output the characteristic of the sample.

BRIEF DESCRIPTION OF THE DRAWINGS

In the course of this description, reference will be made to the attached drawings, wherein like parts denote like parts throughout and wherein:

FIG. 4A is a perspective view of an embodiment of a sensor module. FIG. 4B is a longitudinal cross-sectional view of an embodiment of a sensor module.

DETAILED DESCRIPTION OF THE INVENTION

Before the present optical fiber cartridge assembly is disclosed and described, it is to be understood that this invention is not limited to specific sensor formats, manifold configurations, or analytes as such, of course, may vary. It is also to be understood that the terminology used herein is for the purpose of describing particular embodiments only and is not intended to be limiting.

It must be noted that, as used in the specification and the appended claims, the singular forms "a," "an" and "the" include plural referents unless the context clearly dictates otherwise. Thus, for example, reference to "a sensor module" or includes more than one reference module, reference to a "manifold port" includes more than one such port, and the like.

The invention, together with additional features and advantages thereof, may be best understood by reference to the following description taken in connection with the illustrative drawings.

Figure 1:
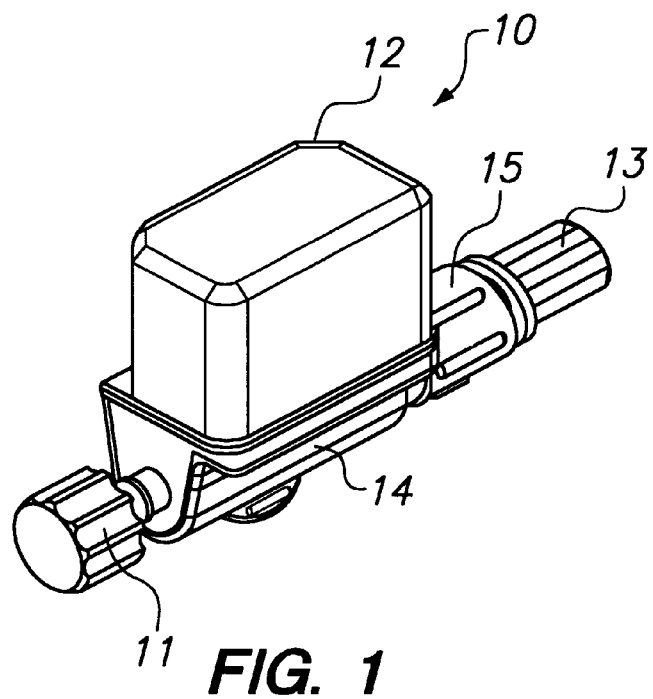
FIG. 1 is an isometric view of one embodiment of the cartridge assembly.
Figure 3:
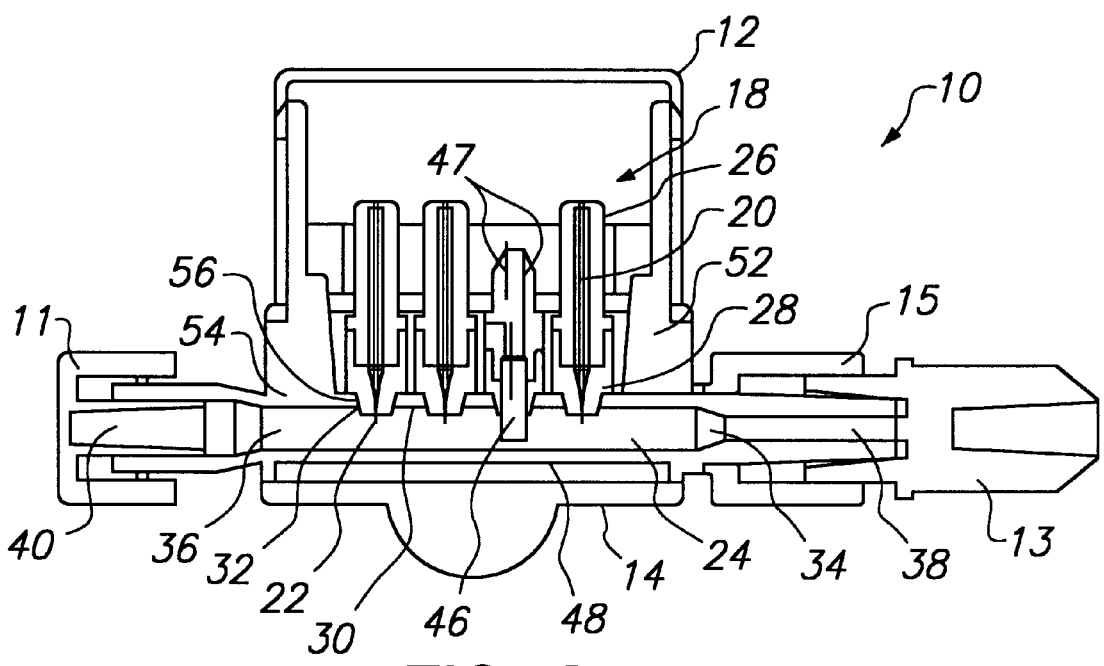
FIG. 3 is a longitudinal cross-sectional view of the cartridge assembly.
Figure 2:
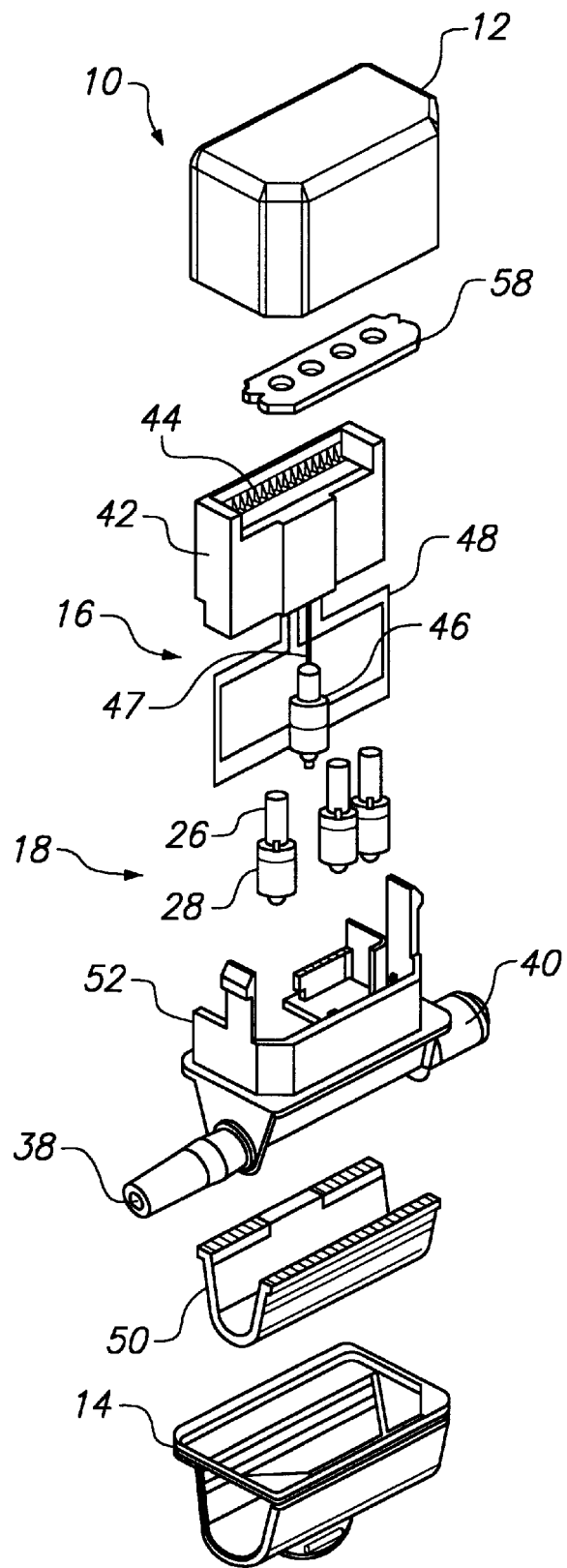
FIG. 2 is an exploded view of the cartridge assembly.

With reference to FIGS. 1 through 3, a preferred embodiment of cartridge assembly 10 is provided for use in a system for analyzing chemical characteristics, for example, $pO_2$, $pCO_2$ or pH, in a physiologic fluid from a human or animal subject. An example of such a system is disclosed in U.S. application Ser. No. 08/379,332, supra. Cartridge assembly 10, an exploded illustration and a longitudinal cross-sectional view of which are depicted in FIGS. 2 and 3, comprises dust cover 12, lower housing 14, which may also serve as a light cover, electronic circuitry assembly 16, and a sensor module 18. Also shown in FIGS. 1 and 3 are plug 11, cap 13 and nut 15 luer fittings.

Sensor module 18 comprises sterile sensor 20 having tip 22 in direct or indirect optical or electrochemical communication with passageway 24 into which the physiologic fluid, or other fluid such as infusion medium or reference sample may be drawn or otherwise introduced, sensor ferrule 26 and sensor gasket 28 (see FIGS. 4A and 4B for additional detail on the sensor module). Passageway 24 contains an interior surface 30, which includes an aperture 32 through which sensor 20 is exposed to the physiologic fluid. The first and second opposing ends of the passageway, respectively indicated at 34 and 36, comprise proximal and distal passageway ports, respectively indicated at 38 and 40, through which movement of fluid into or out of the passageway is effected. Either port may serve as an inlet port, for introduction of fluid into the passageway 24, or an outlet port, for evacuation of fluid from the passageway. Preferably, passageway 24 is placed in fluid communication with a physiologic line and an infusion medium conduit by way of passageway ports 38 and 40 to which can be detachably affixed a flow diversion means, e.g., three-way luer-lock stopcocks, which direct the flow of fluid into or out of the passageway.

A physiologic line and other fluid conduit, e.g., an infusion medium conduit, may be in turn detachably affixed to the flow diversion means. By "physiologic line" is intended any cannula or catheter, one end of which is intended to be situated in a body cavity, duct or vessel so as to permit the withdrawal or injection of fluids. In addition to the cannula or catheter, a physiologic line may include other tubing or conduits associated therewith. Furthermore, a cannula or catheter provides a hollow tube having an interior barrel into which a sensor may be retractably inserted.

Cartridge assembly 10 may include electronic circuitry assembly 16 which comprises circuit board assembly 42, means 44 for providing electronic communication between the cartridge assembly and an instrument that serves as a sensor interface, a read-out means, and the like, through an appropriately sheathed instrument interconnect cable. Cartridge assembly 10 may also include a temperature monitoring means 46, e.g., a thermistor, in thermal communication with passageway 24 to measure the temperature of the physiologic fluid, and heating means 48 by which the temperature of the fluid in the passageway may be regulated. Temperature monitoring means 46 may be exposed to the physiologic fluid in the passageway 24 through an aperture 32 in the interior surface 30 of the passageway. The output from temperature monitoring means 46 and signals by which heating means 48 may be regulated can be communicated with an appropriate instrument by way of the above-described interconnect cable. Cartridge assembly 10 may, optionally, include a cartridge insulating means 50.

Cartridge assembly 10 further comprises assembly body 52 that includes assembly manifold 54 containing manifold port 56 communicating between the cavity formed by the assembly body and aperture 32 in passageway 24, and is adapted to receive and secure sensor module 18 or temperature monitoring means 46. Optionally, passageway 24 is an integral part of assembly body 52 and manifold port 56 is aperture 32 through interior surface 30. Cartridge assembly 10 may also comprise retaining block 58 which serves to secure sensor module 18 and/or temperature monitoring means 46 to assembly body 52.

Sensor 20 which communicates with passageway 24 as described above is preferably a blood gas or pH sensor. However, the invention is not intended to be limited to blood gas and pH sensors. The invention may also be used with sensors such as ionic sensors, glucose sensors, hemoglobin sensors, or the like. Furthermore, the invention is not limited with respect to the sensor format; sensor formats may include optical sensors, electrochemical sensors, and the like. Sensor 20 has a tip 22 which, as illustrated in FIG. 3, extends beyond the interior surface of the passageway into the flow path of the physiologic fluid. Preferably, the tip extends approximately into the center of the flow path. Alternatively, tip 22 may be flush with the interior surface of the passageway.

When an optical sensor format is used in the cartridge assembly, optical sensor module 18 comprises sensor ferrule 26 and sensor ferrule gasket 28. Sensor ferrule 26 may be any single or multiple component assembly used to receive sensor 20, and to position sensor 20 and tip 22 for communication with the fluid in passageway 24. In one preferred embodiment, sensor 20 is an optical fiber sensor having sensing chemistry affixed to tip 22 and sensor module 18 is that described in U.S. Pat. No. 5,216,734, to Grinderslev, supra, and commercially available from Amp, Incorporated (P/N 96-7074-1-1).

Typically, a sensor exhibits a change in sensor read-out (in the case of an optical fiber the change in optical properties of the sensor) when exposed to a reference sample, standard, calibrant or other fluid containing or suspected to contain the analyte to which the sensor is responsive. For optical fiber sensors, the optical properties of chemical sensor compositions typically involve changes in colors, color intensities, or both. A detailed discussion of the preparation and use of optical fiber sensors is provided in U.S. Pat. No. 5,453,248 to Olstein and U.S. Pat. No. 5,607,644 to Olstein et al., both of which are incorporated herein by reference.

An example of a preferred embodiment of sensor module 18 is illustrated in FIG. 4A and FIG. 4B. Sensor module 18 comprises sensor ferrule 26 and sensor ferrule gasket 28. Sensor ferrule 26 has a cylindrical outer wall 60 elongated along axis 62, facet end 64, and back end 66. The exterior dimension of back end 66 is configured to engage sensor ferrule gasket 28, which is designed to seat sensor module 18 in passageway aperture 32 and/or manifold port 56. The outer body is hollowed with an elongated inner cavity 68, preferably substantially cylindrical, that is open at back end 66. The cavity extends for most but not all of the length of the ferrule body. Axially forward of the cavity 68 is a short transition section 70 having funnel-like inwardly tapering walls. A precision passage 72 extends axially from the transition section to the facet end of the ferrule. Passage 72, transition section 70 and cavity 68 form a continuous channel or passage through ferrule body 26, and are concentric with axis 62, as illustrated in FIG. 4B. Outer wall 60 of ferrule body 26 has a chamfer 74 at the facet end 64 thereof. In addition, there is a chamfer 76 at the back end of cavity 68.

Sensor ferrule gasket 28 has facet end 80 and back end 82 may be coupled with back end 66 of ferrule 26 to insure a secure fit (i.e., a gas-tight, water-tight fit that provides a sterile barrier between the passageway and the remainder of the cartridge assembly) with manifold port 56 in assembly manifold 54 in assembly body 52 or with aperture 32 in interior surface 30 of passageway 24. A similar gasket may be used for the same purpose with temperature monitoring means 46.

Sensor ferrule gasket 28 has a substantially cylindrical outer body 84. Facet end 80 of outer body 84 is tapered to fit securely in manifold port 56 or aperture 32. As with ferrule 26, outer body 84 of gasket 28 is hollowed with an elongated inner cavity 86 open at the back end 82 that is designed to securely engage ferrule 26, and tapered bore 88 that terminates in precision passage 90. Cavity 86 extends for a sufficient portion of the length of gasket body 84 to receive and securely engage back end 66 of ferrule 26.

Gasket 28 may be prepared from a silicon-containing polymer such as silicone SE6075 (General Electric), silicone Q7-4780 (Dow), Santoprene® (Monsanto Co., St. Louis, Mo.), Sarlink® 3850 (Novacor Chemicals (Canada) Ltd., Ontario, or DSM Thermoplastic Elastomers Inc., Leominister, Mass.), or the like, other thermoplastic elastomeric materials, or other characteristically rubberlike polymers capable of being injection molded, extruded, blow molded, calendared and thermoformed. Preferably, gasket 28 is prepared from a material that can be compressed to provide a seal when seated in passageway aperture 32 with minimal creep or compression set.

Optionally, sensor 20 may be supported within the ferrule body by a fiber support means 92. Fiber support means 92 may be a hollow sleeve-like insert of, e.g., stainless steel, polymer tubing, or the like, that is slidably assembled to seat, preferably with minimal clearance to insure secure assembly, within cavity 68 of the ferrule body. Alternatively, fiber support means 92 may be curable adhesive, e.g., an two-component epoxy such as available from Epoxy Technology, Inc. (Billerica, Mass.). Fiber support means 92 may extend nearly the entire length of cavity 68 from transition section 70 to the back end 66.

Precision passages 72 and 90 of ferrule 26 and gasket 28, respectively, are dimensioned to support and position the optical fiber therein with precision, as is well known in the art of fiber optic connectors. Any length of optical fiber that protrudes beyond precision passage 72 of ferrule body 26 or passage 90 or gasket 28 may be cleaved to a predetermined length in any conventional manner known to those skilled in the art. A suitable tool used for the cleaving process is described in U.S. Pat. No. 5,018,021, which incorporated herein by reference. Preferably, the optical fiber is terminated at either facet end 64 of ferrule 26 or facet end 80 of gasket 28 using a conventional polishing procedure. More preferably, fiber termination at facet end 64 of ferrule 26 is effected using an angle polishing procedure, thereby insuring the incorporation of a precision gap between the angled terminus of the optical fiber contained in the ferrule and the mated second optical fiber contained in the instrument interconnect cable. Alternatively, the gap may be provided using a spacer between the ferrule and the communicating optical fiber cable contained within the instrument interconnect cable. It is preferred to have an end gap between the optical fiber in the ferrule and the mating optical fiber in the instrument interconnect cable to insure transmission of the light signal from the sensing optical fiber to the communicating cable without wide variation in wavelengths of light being transmitted. In addition, having a gap between the mated optical fibers minimizes physical stresses on the fibers, permitting connect and disconnect without compromising function of the assembly. The gap is preferably about 10 μm to 50 μm in width, more preferably about 20 μm to 30 μm, and most preferably about 25 μm.

The signals from temperature monitor means 46, e.g., through leads 47, to temperature heating means 48 and, where appropriate, electrochemical sensors are passed to the instrument through electronic circuitry assembly 16. The output of assembly 16 is connected by way of interconnect means 44 and by way of an appropriately sheathed communication cable to a read-out means which can be a display, printer or microprocessor which controls additional circuits or calculates analyte levels based on the output of the sensors.

As noted above, cartridge assembly 10 may include temperature monitoring means 46, e.g., a thermistor. One preferred thermistor is a dual thermistor commercially available from, for example, Thermometrics, Inc. The thermistor may be incorporated in an assembly similar to sensor module 18. In other words, the thermistor may be housed in a ferrule/gasket assembly to provide a means whereby the thermistor may be secured to manifold port 56 or aperture 32.

Heating means 48 may be any means by which the temperature of the physiologic fluid in passageway 24 may be regulated. In one preferred embodiment, heating means 48 is a resistance heating element having resistance between about 10 and 50 ohms, preferably between about 15 and 25 ohms, more preferably about 20 ohms. Heating means 48 may be configured to regulate the temperature uniformly throughout passageway 24. An example of a suitable resistance-type heating means is that which is available from Thermal Circuits.

Temperature monitoring means 46 and heating means 48 are connected to circuit board assembly 42, which functions as an electronic interface through which signals for monitoring and regulating the temperature of the fluid contained in the passageway may be communicated via the instrument interconnect means 44. Circuit board assembly 42, is contained within the cavity formed by the assembly body 52.

Cartridge assembly 10 is adaptable to situations in which moisture may be a problem for electronic circuitry assembly 16. Cartridge assembly 10 can be rendered substantially moisture-resistant, thereby insulating electronic circuitry assembly 16 from exposure to moisture, by coating the electronic circuitry assembly with polymeric material such as, for example, a silicone conformal coating, an epoxy-based conformal coating, Parylene (Union Carbide) or the like.

Figure 5:
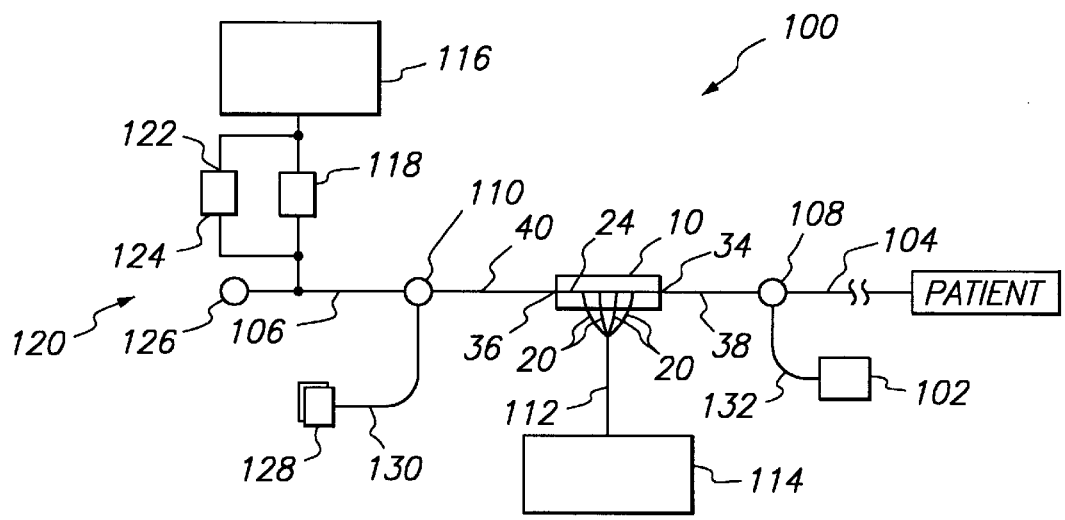
FIG. 5 is a schematic drawing of a first system for monitoring characteristics of a physiologic fluid incorporating a cartridge assembly in accordance with the teachings of the invention.

FIG. 5 illustrates an exemplary installation of the cartridge assembly in a bedside system for monitoring characteristics of a physiologic fluid, for example, $pO_2$, $pCO_2$ or pH, in a physiologic fluid from a human or animal subject, as disclosed in U.S. application Ser. No. 08/379,332, supra. System 100 comprises cartridge assembly 10 including at least one sensor 20 in direct or indirect communication with passageway 24 into which the physiologic fluid, infusion medium or reference sample may be drawn or otherwise introduced. The first and second opposing ends of the passageway, respectively indicated at 34 and 36, comprise proximal and distal ports, respectively indicated at 38 and 40, through which movement of fluid into or out of the passageway is effected. Either port may serve as an inlet port, for introduction of fluid into passageway 24, or an outlet port, for evacuation of fluid from the passageway into optional waste reservoir 102. Passageway 24 is in fluid communication with physiologic line 104 and infusion medium conduit 106 by way of the ports to which are detachably affixed proximal and distal flow diversion means, indicated at 108 and 110, respectively, which direct the flow of fluid into or out of the passageway. Physiologic line 104 and infusion medium conduit 106 are in turn detachably affixed to proximal 108 and distal 110 flow diversion means. The output from the sensors is communicated by an appropriately sheathed communication cable 112 to instrument 114 which acts as a sensor interface and a read-out means.

In this installation of the sensor assembly, physiologic line 104 is an arterial cannula. Additional components of the system which are illustrated in FIG. 5 include a pressurized source of infusion medium 116 which is in fluid communication with infusion medium conduit 106. Interposed between the source of infusion medium and the infusion medium conduit is an infusion medium flow restrictor 118. Fast-flush mechanism 120 is provided to bypass the flow restrictor, wherein the fast-flush mechanism includes a bypass conduit 122 and, incorporated therein, flush valve 124. In communication with the infusion medium conduit is pressure transducer 126 used to monitor the patient's or subject's blood pressure. These additional components are generally provided in an integrated assembly.

A source of a reference sample or calibrant 128 may be provided which is in fluid communication with reference sample conduit 130 to transfer the reference sample from the source to the passageway. This conduit is in fluid communication with flow diversion means 110, by which the reference sample may be introduced into passageway 24 without compromising the sterility of the apparatus. The reference sample or calibrant may be used to conduct in situ sensor calibration and/or quality control checks without compromising sterility of the cartridge assembly.

Optional waste reservoir 102 for disposing of spent reference sample is depicted in FIG. 5. The waste reservoir is in divertable fluid communication with the sensor assembly through a drain conduit 132 which is detachably affixed to a port 38 of cartridge assembly 10 by way of a flow diversion means 108.

In such an installation, arterial blood gas, pH or other analyte values are monitored by drawing a sample of arterial blood into cartridge assembly fluid passageway 24. After allowing sensor 20 to equilibrate with the sample, and after allowing temperature monitoring means 46 and heating means 48 to determine and the adjust the temperature of the sample as needed, a read-out of the sensor is recorded and the $O_2$, $CO_2$ and pH values determined. The blood may then be returned to the patient by activating the fast-flush mechanism or by alternate means, e.g., by flushing passageway 24 using a syringe-flush.

Figure 6:
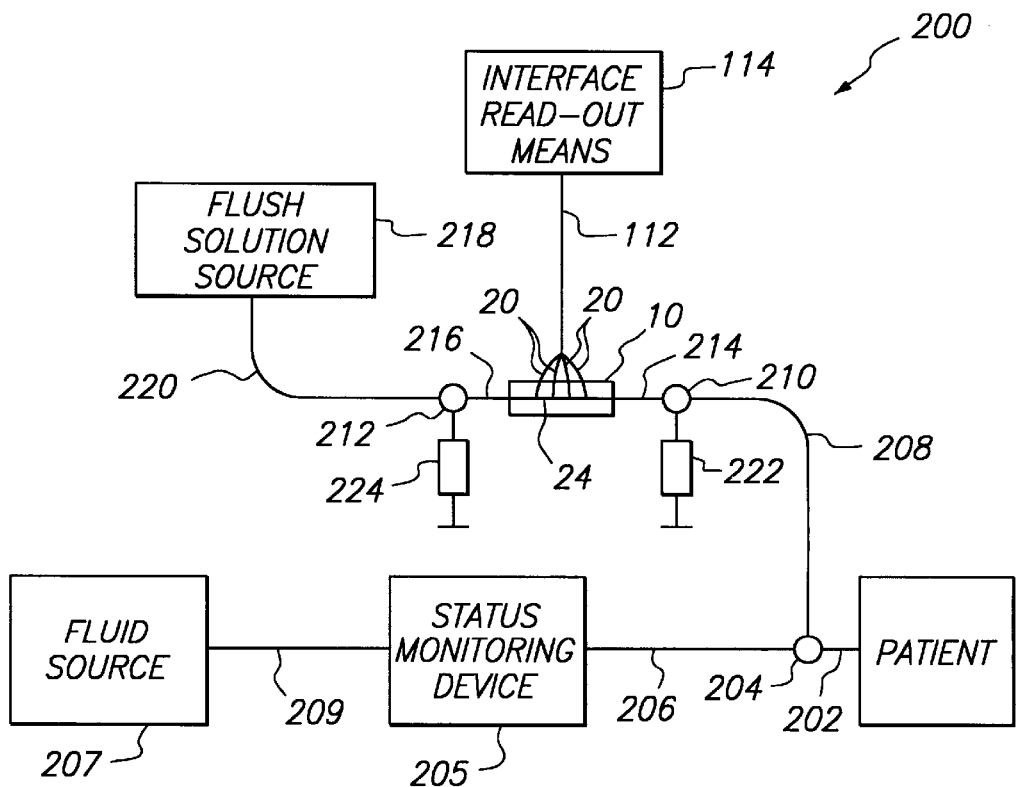
FIG. 6 is a schematic drawing of a second system for monitoring characteristics of a physiologic fluid incorporating a cartridge assembly in accordance with the teachings of the invention.

FIG. 6 illustrates a second exemplary installation of the cartridge assembly in a bedside system which may be adapted for use in, for example, a neonatal subject. When used in a neonatal subject, system 200 comprises an umbilical artery catheter (UAC) 202 detachably affixed to proximal flow diversion means 204 which is in turn detachably affixed to standard physiological status monitoring device 205, such as a pressure sensor, by conduit 206 and to conduit 208, which terminates in medial flow diversion means 210. Fluid source 207 containing, for example, sterile physiologic saline, is detachably affixed to monitoring device 205 by conduit 209. Cartridge assembly 10 with sensor 20 in communication with passageway 24 is detachably affixed to medial flow diversion means 210 and distal flow diversion means 212 by proximal and distal ports, respectively indicated at 214 and 216, through which movement of fluid into or out of the passageway is effected. Either port may serve as an inlet port, for introduction of fluid into passageway 24, or an outlet port, for evacuation of fluid from the passageway. Passageway 24 is optionally in fluid communication with a pressurized source of flush solution 218, e.g., physiologic saline, by conduit 220.

In such an installation, arterial blood gas, pH or other analyte values are monitored by drawing a sample of arterial blood into cartridge assembly fluid passageway 24. In a neonatal installation, syringes 222 and 224 detachably affixed to medial and distal flow diversion means 210 and 212, respectively, are used to draw fluids into and purge fluids from passageway 24. Using procedures well known to those of skill in the art, syringe 222 filled with flush solution is affixed to medial flow diversion means 210 and an empty syringe 224 is affixed to distal flow diversion means 212. The flush solution is then transferred from syringe 222 to syringe 224, thereby flushing passageway 24. Alternatively, if pressurized source of flush solution 218 is attached to distal flow diversion means 212, as illustrated in FIG. 6, and a waste container or empty syringe attached to medial flow diversion means 210, passageway 24 may be flushed by opening the appropriate flow diversion means. In this manner, passageway 24 may be flushed with minimal risk of introducing flush solution into the subject. Once passageway 24 is flushed, a clean syringe can be affixed to distal flow diversion means 212 for drawing blood from the patient into passageway 24. Analyte values are monitored as described above and the blood may or may not be returned to the patient.

Thus, the invention provides a novel cartridge assembly for incorporation into a system for analyzing characteristics of physiologic fluids. Although preferred embodiments of the subject invention have been described in some detail, it is understood that variations can be made without departing from the spirit and the scope of the invention as defined by the appended claims.

It will be appreciated by those working in the art that a cartridge assembly as presently disclosed and claimed may be used in a wide variety of contexts, including measurement of carbon dioxide or other gases, glucose determination, measurement of potassium ions, calcium ions, magnesium ions, and the like. Also, while the invention has primarily been described in conjunction with the measurement of analytes in blood, the cartridge assembly may be used to evaluate a wide range of parameters in any number of sample types.

We claim:

1. A cartridge assembly for use in an in situ system for analyzing a physiologic fluid, comprising:
   an assembly body having
   a) a fluid passageway with an interior surface terminating in distal and proximal passageway ports by which the assembly is removably connected to a physiologic line, thereby forming a flow path through which the physiologic fluid is drawn,
   b) a cavity, and
   c) interposed between the fluid passageway and the cavity, a manifold containing a manifold port that serves as a feedthrough between the cavity and the fluid passageway;
   a sterile optical sensor responsive to a characteristic of the physiologic fluid, wherein said sensor is housed in the cavity of the assembly body and is in fluid communication with the fluid passageway through the manifold port;
   means for monitoring output of the sensor; and
   a resistance-type heating means in thermal communication with the fluid passageway.

2. The cartridge assembly of claim 1, further comprising a temperature monitoring means housed in the assembly body cavity and in thermal communication with the fluid passageway.

3. The cartridge assembly of claim 2, wherein the temperature monitoring means is a thermistor.

4. The cartridge assembly of claim 1, wherein the sensor is an optical fiber sensor contained in a sensor module comprising a sensor ferrule and a sensor gasket coupled to the sensor ferrule, wherein the sensor gasket is designed to engage with the manifold port to provide a gas-tight, watertight seal and a sterile barrier between the fluid passageway and the cavity of the assembly body.

5. The cartridge assembly of claim 4, wherein the sensor has a tip that is flush with the interior surface of the fluid passageway.

6. The cartridge assembly of claim 4, wherein the sensor has a tip that extends beyond the interior surface of the fluid passageway into the flow path.

7. A cartridge assembly for use in an in situ system for analyzing a physiologic fluid, comprising:
   an assembly body having
   a) a fluid passageway with an interior surface terminating in distal and proximal passageway ports by which the assembly is removably connected to a physiologic line, thereby forming a flow path through which the physiologic fluid is drawn,
   b) a cavity, and
   c) interposed between the fluid passageway and the cavity, a manifold containing a manifold port that serves as a feedthrough between the cavity and the fluid passageway;
   a sterile sensor responsive to a characteristic of the physiologic fluid, wherein said sensor is housed in the cavity of the assembly body and is in fluid communication with the fluid passageway;
   a temperature monitoring means housed in the cavity of the assembly body and in thermal communication with the fluid passageway;
   a resistance-type heating means in thermal communication with the passageway; and
   means for monitoring output of the sensor.

8. A method for quantitating an analyte in a sample, comprising:
   (a) providing a cartridge assembly comprising
   an assembly body having
   (i) a fluid passageway with an interior surface terminating in distal and proximal passageway ports by which the assembly is removably connected to a physiologic line, thereby forming a flow path through which the physiologic fluid is drawn,
   (ii) a cavity, and
   (iii) interposed between the fluid passageway and the cavity, a manifold containing a manifold port that serves as a feedthrough between the cavity and the fluid passageway;
   a sterile optical sensor responsive to a characteristic of the physiologic fluid, wherein said sensor is housed in the cavity of the assembly body and is in fluid communication with the fluid passageway through the manifold port;
   means for monitoring output of the sensor; and
   a resistance-type heating means in thermal communication with the fluid passageway,
(b) exposing the sensor to the physiologic fluid, thereby producing a sensor output;
(c) monitoring the sensor output; and
(d) calculating from the sensor output the quantity of the analyte in the sample.

9. The method of claim 8, wherein the cartridge assembly further comprises a temperature monitoring means housed in the assembly body cavity and in thermal communication with the fluid passageway.

10. The method of claim 9, wherein the temperature monitoring means is a thermistor.

11. The method of claim 8, wherein the sensor is an optical fiber sensor contained in a sensor module comprising a sensor ferrule, and a sensor gasket coupled to the sensor ferrule, wherein the sensor gasket is designed to engage with the port to provide a gas-tight, water-tight seal that and a sterile barrier between the fluid passageway and the assembly body cavity.

12. The method of claim 11, wherein the sensor has a tip that is flush with the interior surface of the fluid passageway.

13. The method of claim 11, wherein the sensor has a tip that extends beyond the interior surface of the fluid passageway into the flow path.

\* \* \* \* \*